United States Patent [19]

Nakaso et al.

[11] Patent Number: 5,360,544
[45] Date of Patent: Nov. 1, 1994

[54] DEPROTEINIZATION FILLER AND CARTRIDGE CONTAINING SAME

[75] Inventors: Yasuji Nakaso, Ube; Tsutomu Kawasaki, Tokyo; Wataru Kobayashi, Tsuruoka; Keiko Gondo; Hiroshi Iwase, both of Kawasaki, all of Japan

[73] Assignees: Central Glass Company, Limited, Ube; Koken Co., Ltd.; Moritex Corporation, both of Tokyo, all of Japan; a part interest

[21] Appl. No.: 974,733

[22] Filed: Nov. 13, 1992

[30] Foreign Application Priority Data

Nov. 15, 1991 [JP] Japan .................................. 3-300867

[51] Int. Cl.$^5$ ...................... B01D 24/02; B01D 39/04
[52] U.S. Cl. .................................. 210/483; 210/500.1; 210/503; 210/510.1; 210/198.2; 210/295; 423/306; 423/307; 423/308
[58] Field of Search ...................... 210/767, 500.1, 503, 210/510.1, 198.2, 656, 510.1, 502.1, 483, 295, 306, 307, 308; 423/305, 308, 309, 306, 307; 530/416

[56] References Cited

U.S. PATENT DOCUMENTS

| | | | |
|---|---|---|---|
| 3,737,516 | 6/1973 | Jenner | 423/308 |
| 4,798,886 | 1/1989 | Kato et al. | 530/416 |
| 4,880,610 | 11/1989 | Constantz | 423/305 |
| 5,030,611 | 7/1991 | Ogawa et al. | 423/308 |
| 5,037,543 | 8/1991 | Maejima et al. | 210/510.1 |
| 5,039,408 | 8/1991 | Ichitsuka et al. | 210/656 |
| 5,171,440 | 12/1992 | Kawamura | 210/656 |
| 5,205,928 | 4/1993 | Inoue et al. | 210/198.2 |

FOREIGN PATENT DOCUMENTS 1201015 8/1989 Japan .
3249911 11/1991 Japan .

Primary Examiner—Robert A. Dawson
Assistant Examiner—Ana M. Fortuna
Attorney, Agent, or Firm—Keck, Mahin & Cate

[57] ABSTRACT

A deproteinization filler comprises an aggregate of hydroxyapatite fibers having a three dimensional network structure. The mean radius of pores defined by the aggregate is approximately 0.02 μm to approximately 0.08 μm, the specific surface of the aggregate is approximately 25 m$^2$/g to approximately 65 m$^2$/g and the mean diameter of particles defined by the aggregate is approximately 1 μm to approximately 30 μm. The filler is produced by a given method. The filler may be contained in a throwaway cartridge.

7 Claims, 2 Drawing Sheets

DEPROTEINIZATION FILLER AND CARTRIDGE CONTAINING SAME

BACKGROUND OF THE INVENTION

1. Field of the Invention

The present invention relates in general to deproteinization agents, and more particularly to a deproteinization filler which can remove proteins from a biological sample or the like.

2. Description of the Prior Art

In order to analyze amino acid in biological sample and/or trace the medicinal metabolism of the sample, a so-called "high speed liquid chromatography method" has been used. In fact, such method is widely used in the medical field and the like.

However, in order to deal with a large quantity of biological samples with high accuracy, troublesome and time-consumed analyzing procedure has been hitherto needed even though the high speed liquid chromatography method is used.

One of the reasons of such troublesome and time-consumed procedure is the presence of large quantity of proteins in the samples. That is, proteins have a tendency to interrupt the quantitative analysis for a target constituent in the sample and shorten the life of the analysis instruments. Thus, prior to making the substantive analysis, it is necessary to remove proteins from each sample.

In the medicinal metabolism, for removing proteins, two methods are commonly used, one being a method in which trichloroacetic acid is added to the sample and thereafter a centrifugal separation is carried out on the sample, and the other being a method in which extraction is carried out using organic solvent. However, also these methods require troublesome and time-consumed procedure.

Nowadays, in the field of blood analysis, so-called "blood non-touch analyzing procedure" and "throwaway of tested samples" have been highly desired for avoiding dangerous infection from contaminated blood.

In view of the above, there has been proposed a throwaway type cartridge which has an ultrafilter installed therein. However, in contrast with easier handling of the cartridge, usage of such expensive ultrafilter inevitably brings about increase in production cost of the cartridge. Furthermore, even though such throwaway type cartridge is used, satisfied time saving is not obtained in the analyzing procedure.

As is known, hydroxyapatite is an agent which exhibits a high protein removing ability and thus the agent is used as a column filler when the high speed liquid chromatography method is carried out. In this connection, Japanese Patent Application 2-45297 shows a method for producing a column filler which can remove proteins. In this method, phosphoric acid and calcium hydroxide are reacted to produce a slurry, and the slurry is spray-dried to produce an aggregate of hydroxyapatite. The aggregate is then molded and sintered to form the column filler. However, the column filter produced by this method fails to exhibit a satisfied performance. Japanese Patent First Provisional Publication 1-201015 shows an example in which hydroxyapatite having three dimensional network structure is used as a column filler for the liquid chromatography. That is, the hydroxyapatite is obtained from the reaction between secondary calcium phosphate and alkali. However, this publication fails to describe the protein removing ability which is needed for effectively removing proteins in a very short time.

SUMMARY OF THE INVENTION

In view of the above, various experiments and examinations were carried out by the inventors for the purpose of finding a measure which can eliminate the above-mentioned drawbacks possessed by the prior art.

According to a first aspect of the present invention, there is provided a deproteinization filler which comprises an aggregate of hydroxyapatite fibers having a three dimensional network structure. The mean radius of pores defined by the aggregate is about 0.02 $\mu$m to about 0.08 $\mu$m, the specific surface of the aggregate is about 25 m$^2$/g to about 65 m$^2$/g and the mean diameter of particles defined by thee aggregate is about 1 $\mu$m to about 30 $\mu$m.

According to a second aspect of the present invention, there is provided a throwaway cartridge which contains therein a deproteinization filler, the filler comprising an aggregate of hydroxyapatite fibers having a three dimensional network structure, the mean radius of pores defined by the aggregate being approximately 0.02 $\mu$m to approximately 0.08 $\mu$m, the specific surface of the aggregate being approximately 25 m$^2$/g to approximately 65 m$^2$/g and the mean diameter of particles defined by the aggregate being approximately 1 $\mu$m to approximately 30 $\mu$m.

According to a third aspect of the present invention, there is provided a method for producing a deproteinization agent, which method comprises by steps (a) reacting at least one of $NH_3$, $NH_4OH$, $NaOH$ and $KOH$ with a system which includes secondary calcium phosphate anhydride ($CaHPO_4$) and water; (b) carrying out the reaction keeping the concentration of slurry ($CaHPO_4/H_2O$) within a range from approximately 20% to 60%; and (c) filtering, rinsing and drying the product.

BRIEF DESCRIPTION OF THE DRAWINGS

The detail of the present invention will become apparent from the following description when taken in conjunction with the accompanying drawings, in which.

DETAILED DESCRIPTION OF THE INVENTION

Figure 1:
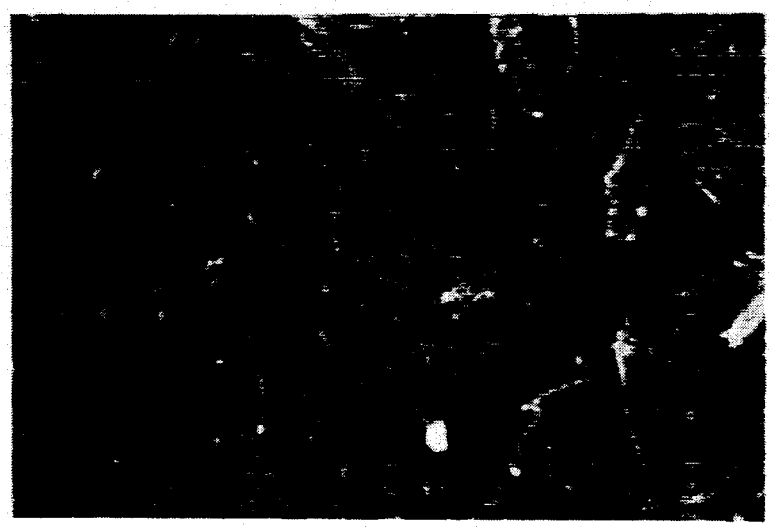
FIG. 1 is a microphotograph showing the outer surface of a deproteinization filler according to the present invention.

FIG. 1 shows, on a large scale, the outer surface of one example (viz., No. 1) of the deproteinization filler according to the present invention. The deproteinization filler is an aggregate of hydroxyapatite fibers of about 0.02 $\mu$m to about 0.07 $\mu$m in length. As is seen from the figure, the hydroxyapatite fibers are complicatedly interwound with one another so that the aggregate has a three dimensional network structure.

The aggregate has a plurality of pores defined by the mutually interwound fibers. The pores have a mean radius of about 0.02 $\mu$m to about 0.08 $\mu$m when measured by using a known mercury penetration pore measuring method.

In order to produce the deproteinization filler of the present invention, the following method is used.

A system consisting of secondary calcium phosphate anhydride ($CaHPO_4$) and water is added with at least one of $NH_3$, $NH_4OH$, $NaOH$ and $KOM$ as alkali, and the reaction of them is carried out keeping the concentration of slurry (viz., $CaHPO_4/H_2O$) within the range from about 20% to about 60%. When the concentration of the slurry is less than 20%, there is produced an aggregate of polycrystalline substance of a structure in which fibrous crystals are roughly interwound with one another and the specific surface of the aggregate is poor, that is, smaller than 25 $m^2/g$. In order to provide the aggregate with a satisfied deproteinizing ability, the specific surface should be higher than 25 $m^2/g$ and thus the concentration of the slurry should be higher than 20%. When the concentration of the slurry exceeds 60%, the reaction solution exhibits marked viscosity making control of the solution difficult and thus it is impossible to produce homogeneous hydroxyapatite fibers.

The mole ratio of Ca/P of the hydroxyapatite thus produced ranges from about 1.4 to about 1.6. Preferably, the particles defined by the hydroxyapatite fibers thus produced have a mean diameter within a range from 1 $\mu m$ to 30 $\mu m$. That is, if the mean diameter is smaller than such range, handling of the hydroxyapatite fibers is difficult, while if the mean diameter is greater than such range, intimate filling in a vessel is not obtained.

The deproteinization filler of the present invention is effective to various types proteins. But, when the filler is used in the field of body fluid of animals, the pores of the filler should have a mean radius of about 0.02 $\mu m$ to about 0.08 $\mu m$. In order to effectively remove Albumin and Globulin, the pores of the filler should have a mean radius of about 0.04 $\mu m$ to about 0.06 $\mu m$. For providing the pores of the filler with such range of mean diameter, the concentration of the slurry (viz., $CaHPO_4/H_2O$) in the reaction should be higher than 20%. When the specific surface of the aggregate is greater than 65 $m^2/g$, the pores of the filler can not have such effective means radius.

Since the deproteinization filler of the invention is of a throwaway type, the same may be put in a cartridge when in use.

Figure 4:
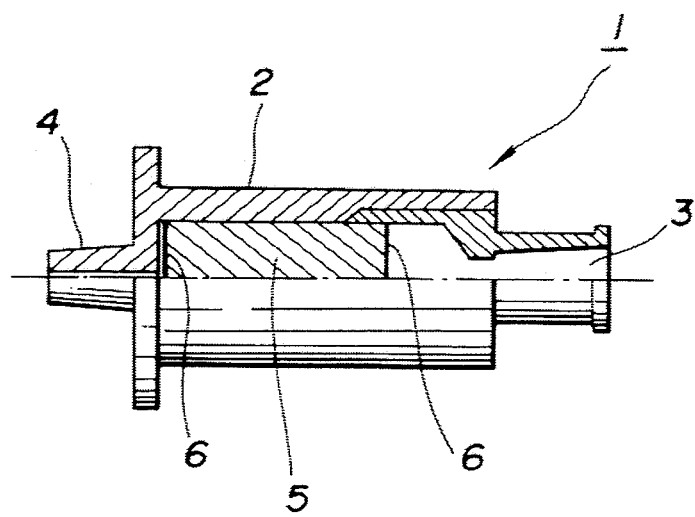
FIG. 4 is a sectional view of a cartridge which has the filler of the present invention contained therein.

FIG. 4 shows the cartridge 1 for the filler, which is designed to contain therein a given amount of the filler 5. Metal, plastic, etc., may be used as the material of the cartridge 1. The cartridge 1 is of a generally cylindrical body which comprises a main cylindrical chamber 2 in which the deproteinization filler 5 is contained, a sample inlet opening 3 into which a protein-possessed liquid sample is introduced and a sample outlet opening 4 from which a protein-removed liquid sample is discharged. Designated by numerals 6 are paper filters between which the filler 5 is positioned. Preferably, the ratio of the length of the main chamber 2 to the diameter of the same is within a range from 1 to 3. The amount of the filler 5 in the cartridge 1 is determined in accordance with the quantity of a test sample which is to be analyzed. At least 1 ml of the filler 5 is preferable when the quantity of the sample is at least 600 $\mu l$. That is, when the amount of the filler 5 is too small, sufficient protein removal from the sample is not expected, while, when the amount of the filler 5 is too large, smoothed flow of the test sample in the cartridge 1 is not expected.

The bulk density of the filler 5 in the cartridge 1 is preferably 1 g/ml. Of course, such density may be varied in accordance with the time which is needed for preparing a desired amount of the test sample which is free of proteins.

As will become apparent as the description proceeds, the protein adsorption filler according to the present invention exhibits an excellent protein removing performance. That is, the filler is substantially 100% efficacious in removing proteins from biological samples and the same shows almost no affect against amino acids in the samples.

In the following, three methods (viz., METHOD-1, METHOD-2 and METHOD-3) which were carried out for producing three types of protein adsorption fillers will be described. It is to be noted that only METHOD-1 is the method for producing the protein adsorption filler according to the present invention.

METHOD-1

7.5 Kg of secondary calcium phosphate anhydride ($CaHPO_4$) and 25 Kg of water were mixed in a reaction vessel of stainless steel (SUS601) and warmed to about 75° C. Then, keeping the PH of the mixture at about 8.0 to about 8.2, 2.5 Kg of 28% $NH_4OH$ was added to the same and the reaction of them was carried out for about 8 hours. After the reaction, the product was filtered, rinsed with sufficient amount of water to remove alkali from the product and dried. With this, the filler example No. 1 (see TABLE-1) was produced. By changing the reaction conditions, the other examples No. 2, No. 3 and No. 4 ( see TABLE- 1) were produced.

The outer surface of the example No. 1 is clearly shown in the microphotograph of FIG. 1. As is seen from this photograph, fibrous members of hydroxyapatite are interwound with one another in a manner to constitute a three dimensional network structure.

METHOD-2

A slurry of calcium hydroxide was added to phosphoric acid solution at room temperature. The reaction therebetween was carried out at about 60° C. for about two hours keeping the slurry concentration at about 5%. The slurry thus produced was spray-dried and baked at about 800° C. With this, a granulated product of hydroxyapatite was prepared.

Figure 2:
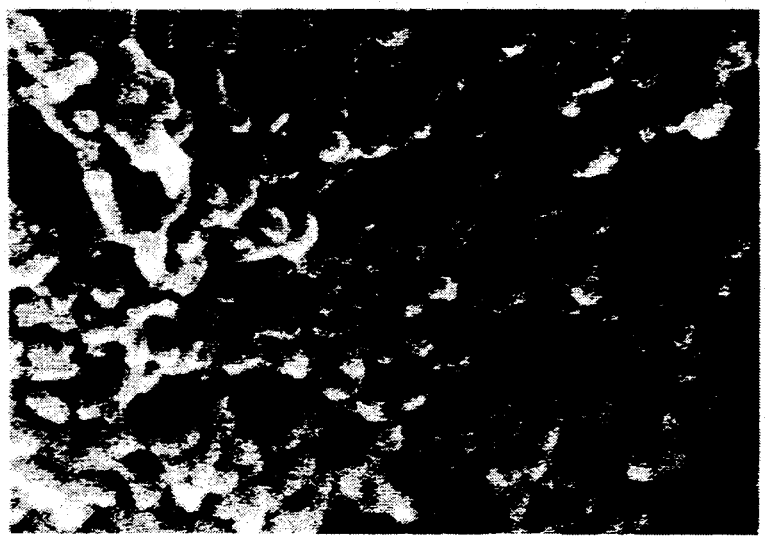
FIG. 2 is a microphotograph showing a first reference filler.

The specific surface of the product was about 22 $m^2/g$ and the mean diameter of particles of the same was about 20 $\mu m$. The outer surface of this product is clearly shown in the microphotograph of FIG. 2. As is seen from this photograph, unlike the filler example No. 1 by the above-mentioned METHOD-1, the product consists of rod-like granules.

METHOD-3

Secondary calcium phosphate and water were mixed to prepare a slurry solution and warmed to about 80° C. A slurry of calcium hydroxide was mixed with the warmed slurry solution keeping the PH of the mixture below 10. The slurry thus produced was spray-dried and baked to produce a granulated product of hydroxyapatite.

Figure 3:
FIG. 3 is a microphotograph showing a second reference filler.

The specific surface of the product was about 7 $m^2/g$ and the mean diameter of particles of the same was about 15 $\mu m$. The outer surface of this product is clearly shown in the microphotograph of FIG. 3. As is seen from this photograph, unlike the example No. 1 by the above-mentioned METHOD-1, the product consists of aggregate of hexagonal crystallized members.

In the following, the performance tests of the above-mentioned products, which were carried out by the inventors, will be described.

EXAMPLE TEST-1

In this test, the protein removing ability of the filler of example No. 1 by METHOD-1 was tested. Using a microspurtle, the filler of example No. 1 was slowly put into a cartridge 1 of the type shown in FIG. 4. The main cylindrical chamber 2 of the cartridge 1 was 9 mm in diameter and 15 mm in length. Using a push rod of 9 mm in diameter, about 0.39 g of the filler of example No. 1 was packed in the main chamber 2 of the cartridge 1. Paper filters (No. 5) were used for positioning the filler.

Then, the cartridge 1, more specifically, the filler example No. 1 was subjected to the performance test using a first biological sample. The first biological sample was produced in the following manner.

A blood serum of cow was diluted with a double amount of demineralized water. The demineralized water was prepared by using the reverse osmosis method and the ion exchanging method. The diluted serum was filtered by a membrane filter of 0.45 μm in pore size. With this, the first biological sample was prepared.

Just 2 ml of the filtered diluted serum was put into a glass syringe. The syringe was connected to the sample inlet opening 3 of the cartridge 1, and then, the diluted serum in the syringe was slowly injected into the cartridge 1. After one minute twenty seconds from the injection start, a first drop of the cartridge-passed sample appeared at the sample outlet opening 4 of the cartridge 1, and subsequent drops followed every ten seconds thereafter. After two minutes fifty seconds from the injection start, the sample injection was stopped. The drops were then subjected to an examination for measuring a protein removing ability of the tested fillers.

The examination was carried out by using an absorptiometric method. That is, for this examination, the phenomenon wherein the color tone of a certain coloring matter is changed due to coupling with proteins is practically used. A proteinase reagent produced by Biorad Company was used and the absorptiometer was set to measure the absorption at 595 nm in wave length.

The examination revealed that the first to eighth drops of the sample had removed the proteins therefrom by about 98%. These eight drops were sufficient for preparing a test sample used in the high speed liquid chromatography method. In fact, for precisely analyzing amino acid, the amount of the test sample must be 0.2 ml (corresponding to the amount of five drops) at the least.

EXAMPLE TEST 2, EXAMPLE TEST-3 & EXAMPLE TEST-4

Examples Nos. 2, 3 and 4 by METHOD-1 were also subjected to the same performance test by using the same procedure and method as those of the above-mentioned EXAMPLE TEST-1. The performance test revealed that, also in these examples (viz., No. 1, No. 2 & No. 3), the first to eighth drops of the sample had removed the proteins therefrom by about 98%.

In order to clarify the superior performance of the examples Nos. 1, 2, 3 & 4 by METHOD-1, reference performance tests were also carried out on the products by METHOD-2 and METHOD-3.

REFERENCE TEST-1

The product by METHOD-2 was subjected to the same performance test using the same procedure and method as those of the above-mentioned EXAMPLE TEST-1. The performance test revealed that the second drop of the cartridge-passed sample had removed the proteins therefrom by about 97% and the third drop had removed the same by about 91%. That is, the protein removing ability of the product by METHOD-2 was insufficient.

REFERENCE TEST-2

The product by METHOD-3 was subjected to the same performance test. The test revealed that the third drop had removed the protein therefrom by about 97% and the fourth drop had removed the same by about 94%. The protein removing ability of the product by METHOD-3 was also insufficient.

EXAMPLE TEST-5

In this test, a so-called "amino acid passing property" of the example No. 1 by METHOD-1 was tested. The filler example No. 1 was put into the cartridge 1 in the same manner as that of EXAMPLE TEST-1. A second biological sample was used, which was produced by mixing one part of standard solution of amino acid (2 mg/dl) and three parts of 10 mM buffer solution of sodium phosphate (PH 7.7). Just 2 ml of the second biological sample was injected into the cartridge 1 by using a glass syringe. The cartridge-passed sample from the sample output opening 4 was subjected to an amino acid recovery test by using a known ninhydrin reaction method. For this test, Asahipak G-520 (50×0.7 cm i.d.) was used under a condition wherein the detecting wave length is 250 nm, the moving phase is the PH 7.0 solution comprising 30 mM of sodium phosphate and 150 mM of sodium sulfate and the flow velocity is 1 mM/min.

The result of this test is shown in TABLE-2. As is seen from the table, the example No. 1 by METHOD-1 had substantially no affect on amino acids.

EXAMPLE TEST-6

In this test, human blood plasma was used as a third biological sample for testing the filler example No. 1. For this test, the same procedure and method as those described in EXAMPLE TEST-1 were carried out.

The result of this test is shown in TABLE-3.

EXAMPLE TEST-7

In this test, a fourth biological sample was used for testing the filler example No. 1. The fourth biological sample was produced by mixing 50 μl of blood serum, 450 μl of demineralized water, 500 μl of physiological salt solution, 20 μl (50 ppm) of Theophylline (viz., medicine for bronchial asthma) and 10 μl (100 ppm) of 7-(2-Hydroxyethyl) theophylline (1S) (viz., internal standard substance). The example No. 1 was put in the cartridge 1 and the fourth biological sample was injected into the cartridge 1. The cartridge-passed sample was subjected to a theophylline recovery test by using a high speed liquid chromatography equipment. About 92.9% of the theophylline was recovered.

The operating condition of the chromatography equipment was as follows.

Detecting wave length: 280 nm
Column: Inertsil ODS, 0.46 i.d. ×15 cm
Moving phase: 10 parts of acetonitrile+90 parts of water
Flow velocity: 1 ml/min
Amount of injected sample: 20 μl As is understood from the foregoing description, the deproteinization filler according to the present invention can effectively remove proteins from a biological sample. When the deproteinization filler is packed in a cartridge as shown in FIG. 4, easy and sanitary handling of the same is assured.

TABLE 1

| | CHARGE | | SLURRY CONCENTRATION (%) | REACTION TEMPERATURE (°C.) | pH | REACTION TIME (Hr) | SPECIFIC SURFACE ($m^2/g$) | MEAN RADIUS OF PORES (μm) | Ca/P |
|---|---|---|---|---|---|---|---|---|---|
| No. 1 | $CaHPO_4$ | 7.5 Kg | 23 | 75 | 8.2 | 8 | 53 | 0.04 | 1.55 |
| | $H_2O$ | 25 Kg | | | | | | | |
| | 28% $NH_4OH$ | 2.5 Kg | | | | | | | |
| No. 2 | $CaHPO_4$ | 7.5 Kg | 20 | 75 | 8.2 | 8 | 35 | 0.05 | 1.55 |
| | $H_2O$ | 30 Kg | | | | | | | |
| | 28% $NH_4OH$ | 2.5 Kg | | | | | | | |
| No. 3 | $CaHPO_4$ | 7.5 Kg | 23 | 50 | 8.2 | 13 | 40 | 0.05 | 1.42 |
| | $H_2O$ | 25 Kg | | | | | | | |
| | 20% NaOH | 5.8 Kg | | | | | | | |
| No. 4 | $CaHPO_4$ | 7.5 Kg | 25 | 75 | 8.4 | 4 | 33 | 0.06 | 1.44 |
| | $H_2O$ | 22 Kg | | | | | | | |
| | 20% NaOH | 4.1 Kg | | | | | | | |

TABLE 2

| AMINO ACID | RECOVERY (%) |
|---|---|
| Gly | 87.7 |
| Ala | 97.2 |
| Val | 101 |
| Leu | 101 |
| Ile | 102 |
| Pro | 101 |
| Thr | 90.4 |
| Met | 97.7 |
| Phe | 101 |
| Tyr | 99.4 |
| Arg | 90.4 |
| His | 93.4 |
| Asp | 87.5 |
| Glu | 99.2 |

TABLE 3

| BUFFER SOLUTION | pH | RATIO BETWEEN BLOOD PLASMA & BUFFER SOLUTION | 1'st FRACTION | | 2'nd FRACTION | | 3'rd FRACTION | |
|---|---|---|---|---|---|---|---|---|
| | | | ALBUMIN | GLOBULIN | ALBUMIN | GLOBULIN | ALBUMIN | GLOBULIN |
| 50 mM Na | 7.7 | 1:1 | 0 | 0 | 17.79 | 29.81 | 34.99 | 27.54 |
| 10 mM Na | 7.7 | 1:1 | 0 | 0 | 2.07 | 35.37 | 62.66 | 61.95 |
| 10 mM Na | 7.7 | 1:3 | 0 | 0 | 0 | 0 | 0.15 | 0.18 |
| 10 mM K | 7.7 | 1:3 | 0 | 0 | 0 | 0 | 8.91 | 18.09 |
| 10 mM $NH_4$ | 7.7 | 1:3 | 0 | 0 | 0 | 0 | 12.72 | 31.26 |
| 10 mM Na | 7.7 | 1:9 | 0 | 0 | 0 | 0 | 0 | 0 |

NOTE:
50 mM Na: BUFFER SOLUTION ADJUSTED BY 50 mM SODIUM PHOSPHATE.
10 mM Na: BUFFER SOLUTION ADJUSTED BY 10 mM SODIUM PHOSPHATE.
10 mM K: BUFFER SOLUTION ADJUSTED BY 10 mM POTASSIUM PHOSPHATE.
10 mM NH4: BUFFER SOLUTION ADJUSTED BY 10 mM AMMONIUM PHOSPHATE.
EACH FRACTION CONTAINS 300 μl AND EACH NUMERAL IN FRACTION SECTION DENOTES CONTENT (%) OF CORRESPONDING PROTEIN
TEST SAMPLE: 2 ml

What is claimed is:

1. A deproteinization filler comprising an aggregate of hydroxyapatite fibers having a three dimensional network structure, wherein the mean radius of pores defined by said aggregate is approximately 0.02 μm to approximately 0.08 μm, the specific surface area of said aggregate is approximately 25 $m^2/g$ to approximately 65 $m^2/g$ and the mean diameter of particles defined by said aggregate is approximately 1 μm to approximately 30 μm.

2. A deproteinization filler comprising an aggregate of hydroxyapatite fibers having a three-dimensional network structure, wherein the mean radius of pores defined by said aggregate is approximately 0.02 μm to approximately 0.08 μm, the specific surface area of said aggregate is approximately 25 $m^2/g$ to approximately 65 $m^2/g$ and the mean diameter of particles defined by said aggregate is approximately 1 μm to approximately 30 μm; wherein the hydroxyapatite fibers have a mean length of approximately 0.02 m to 0.07 m.

3. A deproteinization filler as claimed in claim 2, in which the hydroxyapatite fibers are complicatedly interwound with one another.

4. A deproteinization filler as claimed in claim 2, in which the mean radius of pores defined by said aggregate ranges from approximately 0.04 μm to 0.06 μm.

5. A throwaway cartridge containing therein a deproteinization filler, said filler comprising an aggregate of hydroxyapatite fibers having a three dimensional network structure, the mean radius of pores defined by said aggregate being approximately 0.02 μm to approximately 0.08 μm, the specific surface area of said aggregate being approximately 25 $m^2/g$ to approximately 65 $m^2/g$ and the mean diameter of particles defined by said aggregate being approximately 1 μm to approximately 30 μm.

6. A throwaway cartridge containing therein a deproteinization filler, said filler comprising an aggregate of hydroxyapatite fibers having a three-dimensional network structure, the mean radius of pores defined by said aggregate being approximately 0.02 μm to approximately 0.08 μm, the specific surface area of said aggregate being approximately 25 m$^2$/g to approximately 65 m$^2$/g and the mean diameter of particles defined by said aggregate being approximately 1 μm to approximately 30 μm, wherein the amount of the filler in the cartridge is approximately 1 ml.

7. A throwaway cartridge containing therein a deproteinization filler, said filler comprising an aggregate of hydroxyapatite fibers having a three-dimensional network structure, the mean radius of pores defined by said aggregate being approximately 0.02 μm to approximately 0.08 μm, the specific surface area of said aggregate being approximately 25 m$^2$/g to approximately 65 m$^2$/g and the mean diameter of particles defined by said aggregate being approximately 1 μm to approximately 30 μm, wherein the bulk density of the filler in the cartridge is approximately 1 g/ml.

* * * * *